United States Patent [19]

Pedersen

[11] 3,987,061
[45] Oct. 19, 1976

[54] MACROCYCLIC POLYETHER COMPOUNDS

[75] Inventor: Charles J. Pedersen, Salem, N.J.

[73] Assignee: E. I. Du Pont de Nemours and Company, Wilmington, Del.

[22] Filed: Feb. 15, 1974

[21] Appl. No.: 442,909

Related U.S. Application Data

[63] Continuation of Ser. No. 106,565, Jan. 14, 1971, abandoned.

[52] U.S. Cl. .................... 260/340.2; 260/340.3; 260/327 B; 260/448.8 R; 260/429.7
[51] Int. Cl.² .................................. C07D 323/00
[58] Field of Search ................ 260/340.3, 340.2

[56] References Cited
UNITED STATES PATENTS 3,687,978  8/1972  Pederson ............... 260/340.3

OTHER PUBLICATIONS

Pederson IV, J.A.C.S. 92, pp. 391–394, (Jan. 28, 1970).
Pederson II, JACS, 89, (1967), pp. 7017–7035.
Pederson III, Chem. Abst., 72:66915v, (1970).

Primary Examiner—Lorraine A. Weinberger
Assistant Examiner—Michael Shippen

[57] ABSTRACT

Macrocyclic polyether "crown" compounds of the formula

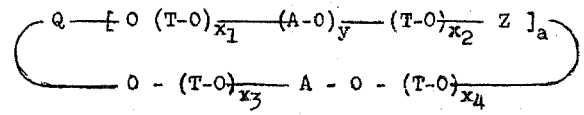

wherein T is a $C_2$–$C_3$ alkylene, A is

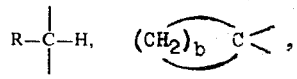

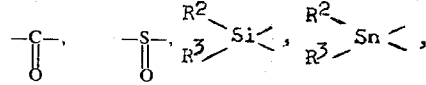

R being H or $C_1$–$C_{18}$ alkyl, $R^2$ and $R^3$ being independently $C_1$–$C_{18}$ alkyl, $C_2$–$C_4$ alkenyl, or $C_6$–$C_{14}$ aryl; Q and Z are independently 1,2-arylene (or saturated derivatives thereof) or substituted 1,2-arylene (or saturated derivatives thereof); $a$ is 0, 1, 2, or 3; $b$ is an integer from 3 to 20; $y$ is 1 or zero; $x_1$, $x_2$, $x_3$, and $x_4$ are integers independently selected to give a 15–60 atom ring. Such crown compounds are generally useful in the formation of complexes with ionic metal compounds, thus making it possible to use certain chemical reagents in media wherein they are normally insoluble.

3 Claims, No Drawings

MACROCYCLIC POLYETHER COMPOUNDS

REFERENCE TO PRIOR FILED APPLICATION

This application is a continuation of Application Ser. No. 106,565 filed January 14, 1971, now abandoned.

BACKGROUND OF THE INVENTION

Heretofore, many chemical reagents useful in aqueous and alcoholic media have been unavailable for use in non-hydroxylated media wherein they are normally insoluble. For example, although potassium hydroxide is a commonly employed reagent and benzene a widely used solvent, it has not been possible to dissolve the former in the latter even though finely divided potassium hydroxide is vigorously stirred into boiling benzene. Again, though potassium permanganate is widely used as an oxidizing agent, it has not been possible to employ the same to oxidize, e.g. olefinic compounds in hydrocarbon media because of its insolubility therein. Sodium nitrite, a corrosion inhibitor of iron and steel in aqueous systems, has not heretofore been susceptible to that employment in non-aqueous systems. Thus, a need has existed for a means of carrying normally insoluble reagent substances into solution in non-hydroxylic media.

Cyclic polyethers having four or more oxygen atoms in the polyether ring have been prepared heretofore. A review of the pertinent literature is set out in C. J. Pedersen, J. Am. Chem. Soc. 89, 7017 (1967). In none of the literature reviewed is mention made of formation of stable complexes of the subject cyclic polyethers with salts of ionic metals such as alkali and alkaline earth metals.

THE INVENTION

According to this invention there are provided macrocyclic polyether compounds. Generally, these compounds can form complexes with the cations of metal compounds, particularly ionic alkali metal and alkaline earth metal compounds. Such complexes are new analytical reagents for use in non-hydroxylated media wherein the uncomplexed metal compounds are normally insoluble.

Macrocyclic polyether compounds of the invention have from 15 to 60 ring atoms in the polyether ring and are compounds of the formula

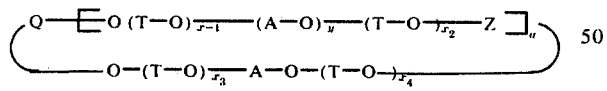

wherein T is $C_2$–$C_3$ alkylene; A is

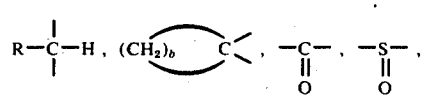

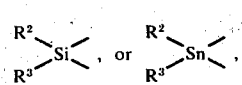

R being H or $C_1$–$C_{18}$ alkyl, $R^2$ and $R^3$ being independently $C_1$–$C_{18}$ alkyl, $C_2$–$C_4$ alkenyl, or $C_6$–$C_{14}$ aryl; Q and Z are independently 1,2arylene (or saturated derivatives thereof) or substituted 1,2-arylene (or saturated derivatives thereof), typical substituents being, for example, alkyl, aryl, aralkyl, alkaryl, alkoxy, halo, —CN, carboxy, and carbethoxy, preferred substituents are 1,2-phenylene and 1,2-cyclohexylene; $a$ is 0, 1, 2, or 3; $b$ is an integer from 3 to 20; $y$ is 1 or zero; $x_1$, $x_2$, $x_3$, and $x_4$ are integers independently selected to give a 15–60 atom ring.

Molecular models of representative compounds of the present invention have an annular configuration suggestive of a crown, and accordingly, the macrocyclic polyethers of the present invention are denoted "crown" compounds. Complexes of these compounds with ionic metal compounds are denoted "crown" complexes.

The macrocyclic compounds of the present invention, in the broadest description, are polyether rings having from 15 to 60 atoms in the ring and containing within ring one or more additional groups selected from the group herein before defined by A. The ring carbon atoms can be alkyl-substituted by alkyl groups of about 1–4 carbon atoms. Preferably, alkyl substituents are $C_1$–$C_2$ to reduce stearic hindrance in complexing. The preferred maximum number of ring atoms is 30.

Preferred compounds within the scope of this invention in that they tend to be superior complexing agents are the macrocyclic polyether compounds hereinbefore described wherein T is $C_2$ alkylene; $y = 0$; A is

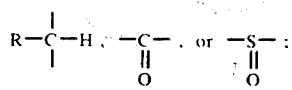

and wherein the polyether ring contains about 20 atoms.

Especially good complexing agents are macrocyclic polyether compounds of the following formulas:

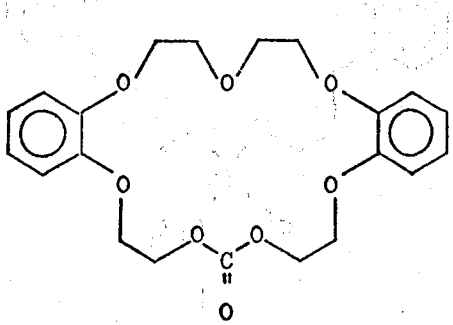

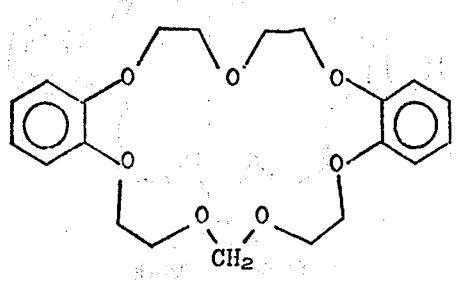

Typical of the crown compounds of this invention are:
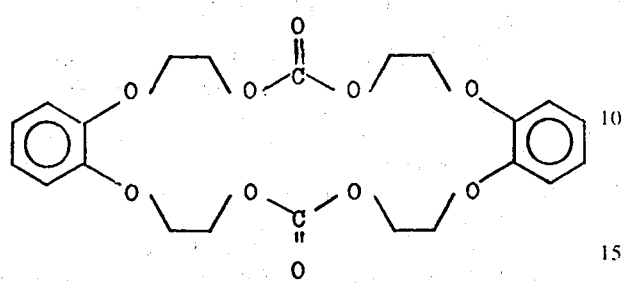
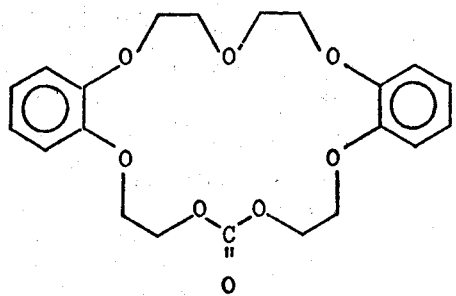
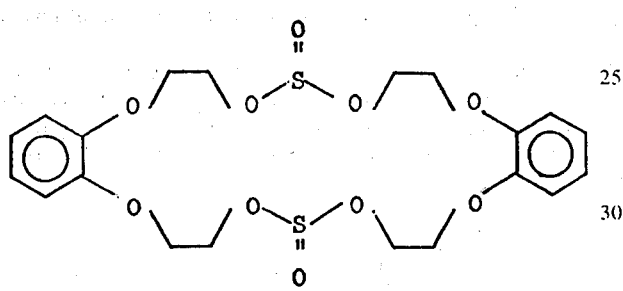
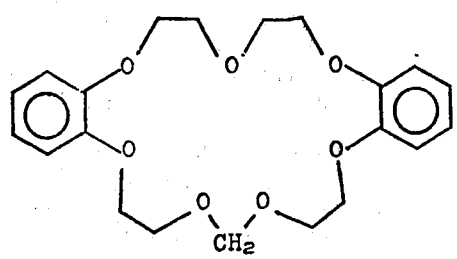
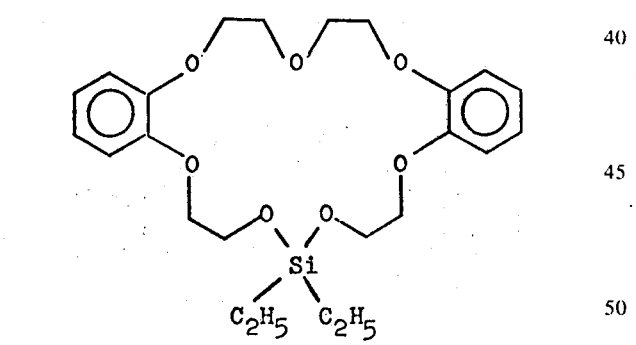
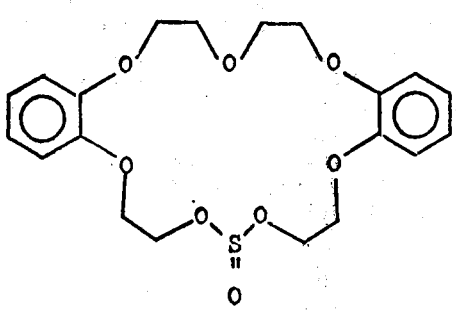
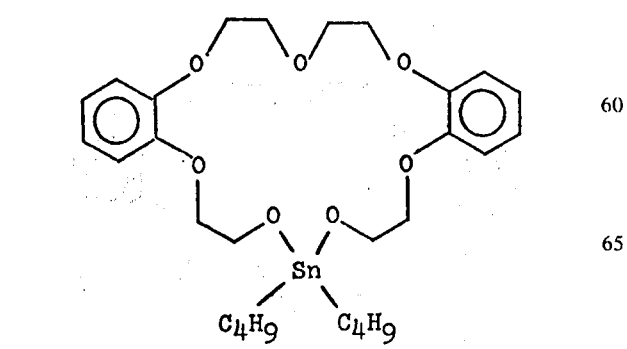
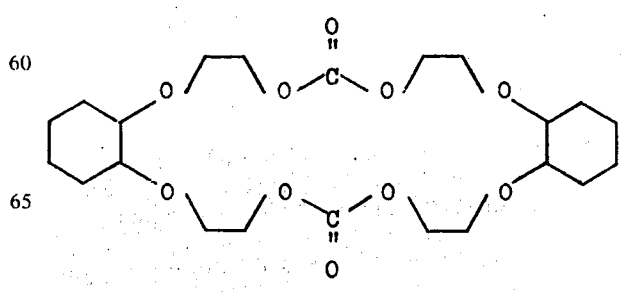

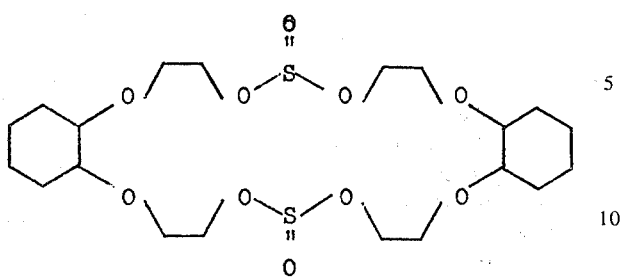

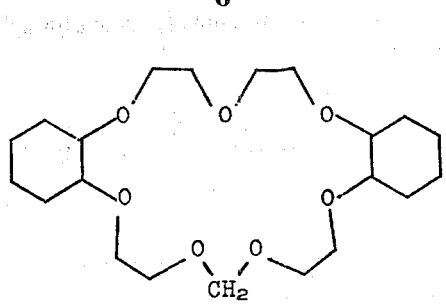

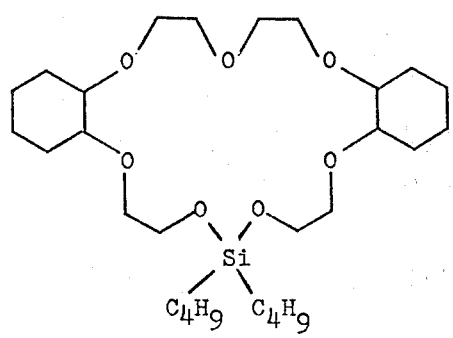

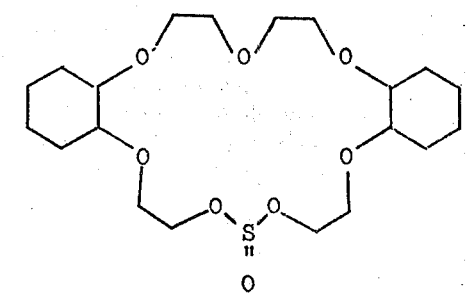

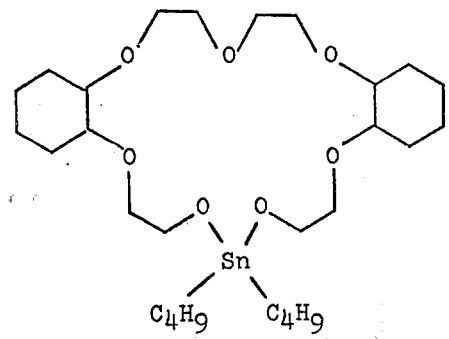

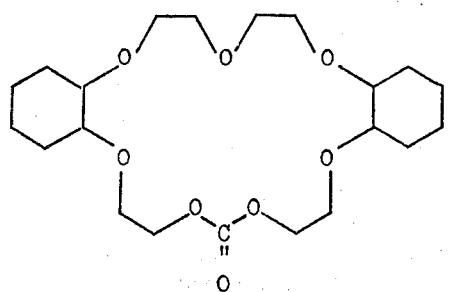

The crown compounds of the present invention are generally made by a sequence of reactions patterned to produce a heterocyclic ring having the desired size and configuration and fused to carbocyclic rings of the proper type and substitution. Undesired side reactions are minimized by employing protective groups to inactivate sites which can compete with the desired ones, by selecting reaction media in accordance with the criteria given below, and by doing any needed hydrogenations before the A groups are present.

In general, an A group can be introduced by reacting a simple reagent having no polyether groups, e.g., $CH_2Cl_2$, $COCl_2$, $SOCl_2$, $R^2R^3SnCl_2$, $R^2R^3SiCl_2$, HCHO, R'CHO, and $(CH_2)_{3-20}$ C=O, with hydroxyalkylene groups; thus

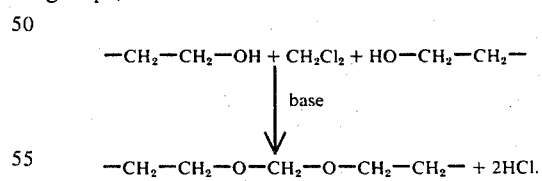

The diorganometal dichlorides behave analogously. Further,

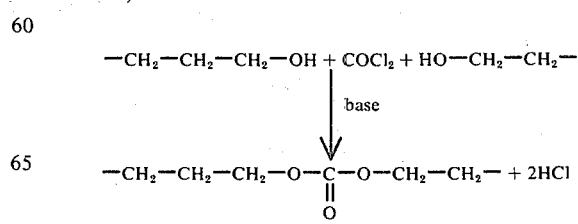

Thionyl chloride reacts similarly. When formaldehyde is employed

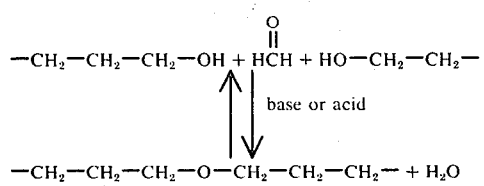

Aldehydes and the cyclic ketones give acetals and ketals, respectively.

The base used in these preparations varies according to the reaction. The best base for $SOCl_2$ and $COCl_2$ is an amine (primary, secondary or tertiary); aqueous base will give lower yields. $R_2R_3SiCl_2$ requires an amine; aqueous bases will not work at all. $R_2SnCl_2$ can use amines or aqueous base. The aldehydes and cyclic ketones are reacted in the presence of acids such as p-toluenesulfonic acid, or aqueous alkali (or alkaline earth) metal hydroxides such as KOH; the latter aqueous bases are also suitable for $CH_2Cl_2$.

The A group can also be part of a ring bridging element. For example,

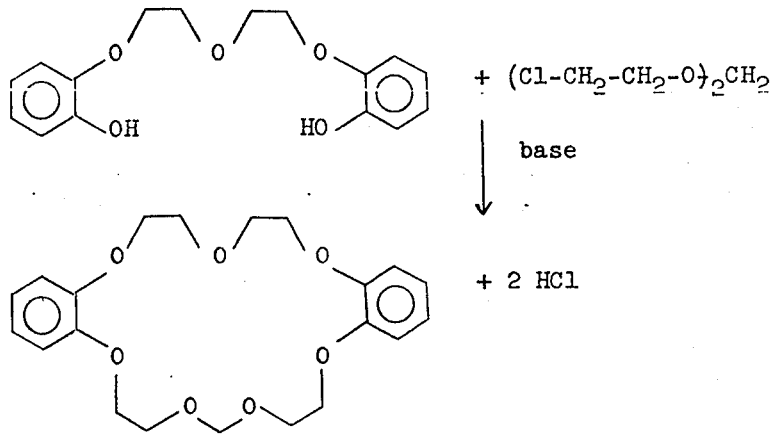

Reactants such as $(Cl-CH_2-CH_2-O)_2S=O$ and $(Cl-CH_2-CH_2-O)_2C=O$ will introduce the respective $$-\overset{O}{\underset{\|}{S}}- \quad \text{and} \quad -\overset{O}{\underset{\|}{C}}-$$

A groups.

The polyether portion of the crown compound can be built up from reactants having a benzenoid nucleus (or saturated analog thereof) to which a pair of hydroxyl groups are vicinally attached, as in catechol

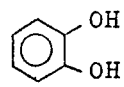

or 1,2-cyclohexanediol

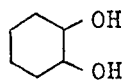

If a crown having a single carbocyclic fused nucleus is desired, a bridging group is built up from one of the vicinal groups and joined to the other vicinal group, or a complete bridging group is attached first to one vicinal group and then to the other. If a crown having two carbocyclic fused nuclei is desired, there are several general methods. In one procedure, a bridging group is attached to (or built up from) one vicinal group on a benzenoid nucleus; then two of these compounds are codimerized, each compound supplying one bridging group which joins the free vicinal group of the other to form the macrocyclic ring. In an alternative procedure, a pair of benzenoid nuclei are bridged; then the ends of a bridging group are attached to the free vicinal groups (one on each nucleus) to form the macrocyclic ring. If a crown having more than two carbocyclic fused nuclei is desired, the needed benzenoid nuclei are bridged in a linear manner to give a polymer having terminal benzoid nuclei bearing one free vicinal group apiece; a bridging group is then attached to these free vicinal groups to form the macrocyclic ring.

When a vicinal dihydroxy aromatic compound such as catechol is employed as the starting point, the crown system of this invention can be formed in a variety of ways making use of the Williamson ether synthesis. A salt of the organic hydroxy compound is reacted with a primary halide

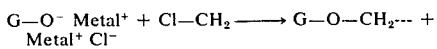

General approaches and specific details of crown synthesis are given in J. Am. Chem. Soc. 89, p. 7017 et seq. (1967) and in British Patent 1,149,229.

When a crown compound of this invention is to have a saturated carbocyclic ring, it can be built up from a saturated carbocyclic vicinal diol, such as 1,2-cyclohexanediol, by reacting it with a sulfonate in the presence of a base in a polar aprotic solvent. Preferably tosylates are used

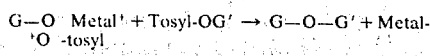

Preferred bases are alkali metal hydrides (e.g., LiH), alkali metal hydroxides (e.g., NaOH), or metal tertiary alkoxides (e.g., K tert-butoxide). Typical solvents include diethyl ether, tetrahydrofuran, dimethyl formamide, and dimethyl sulfoxide. Temperatures ranging from room temperature to about the boiling point of the solvent are useful.

It will be evident that classical organic chemical procedures may have to be employed on occasion to protect one or more functional groups present, e.g., one of a pair of vicinal hydroxyl groups. Representative protecting groups for hydroxyl are benzyl, tetrahydropyranyl, methoxymethyl, trityl, and tert-butyl carbobenzoxy. Procedues for protecting functional groups are well summarized in *Advances in Organic Chemistry*, Vol. III, Interscience Publishers, N.Y., 1963, pages 159–294. British Pat. No. 1,149,229 illustrates the use of protective groups in building polyether crowns; these teachings are applicable here.

At one or more stages in the synthesis of the crown compounds of the present invention a chain-lengthening reaction may be required. The reaction of ethylene oxide with G-OH, an organic compound having a hydroxyl group, gives the following result

where $n = 1, 2, \ldots$ The analogous reaction of oxacyclobutane

forms $G-O-(CH_2-CH_2-CH_2-O-)_nH$. The spacing between the oxygen atoms in the heterocyclic ring containing divalent group A can thus be arranged as desired.

The solvents employed for making the crown compounds of this reaction should not interfere with the reaction or adversely affect the crown compound; preferably the solvents should dissolve both the reactants and the product.

When the A group is introduced by an aldehyde, a cyclic ketone, phosgene, thionyl chloride, or a diorganotin dichloride, the solvent (or diluent) can be an aromatic hydrocarbon (such as benzene, toluene, and mixed xylenes), an ether (such as 1,4-dioxane, tetrahydrofuran, a lower alkyl diether derivative of ethylene glycol, such as 1,2-dimethoxyethane, which is preferred, and a lower alkyl diether derivative of a polyethyleneeether glycol having a normal boiling point below 150° C.), and water; alcohols should be absent. When a diorganodihalosilane is employed, water is also excluded from the above list. When methylene chloride and reactants having terminal —CH$_2$Cl group are employed, both water and alcohols (e.g., butanol) can be used (as well as the ethers and hydrocarbons mentioned above). The amount of solvent needed can be selected on the basis of operating convenience for a particular set of reactants.

The reactions can be carried out over a wide range of temperatures. For operating convenience, temperatures from about 60° C. to about 140° C. are preferred. The reaction time will vary depending upon the temperature and other factors. Other conditions being equal, the higher the temperature the shorter the time. Typically, time can range from about 6 hours to about 24 hours. The most suitable time and temperature for particular reactants can be determined by routine experimentation.

The crown compound can be isolated by conventional methods such as by concentration of the reaction mixture, chromatographic separation, and mechanical collection of insoluble (or precipitated) product. The crown compounds are chromatographed on acid-washed alumina or silica gel which retains hydroxylated open chain polyethers; the crown is eluted with readily volatile hydrocarbons such as heptane. Identification of the crown compounds is based on elementary C,H,O analysis, molecular weight and nmr spectra. Recrystallization of the purified product can be undertaken to improve its crystalline form. Infrared spectrum can be employed for confirmation.

Carbocyclic nuclei or rings which are vicinally fused to a macrocyclic ring in the crowns are selected from the group consisting of monocyclic and polycyclic aromatic hydrocarbons of the benzo series consisting of from 1 to 3 fused rings (benzene, naphthalene, anthracene, phenanthrene), and the perhydro analogs thereof. The nuclei can be represented as R-substituted, i.e.,

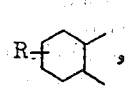

where R is hydrogen, halo, nitro, nitroso, amino, azo, $C_1$–$C_4$ alkyl, $C_1$–$C_4$ alkenyl, $C_6$–$C_{12}$ aryl, $C_7$–$C_{16}$ aralkyl, $C_1$–$C_4$ alkoxy, cyano, hydroxy, carboxy, sulfo and the like and can be attached to any of the available ring positions. Provided the substituent group is stable with the reactants employed in forming the novel crowns of the invention, the group can be present in the vicinally difunctional compounds which are preferred starting materials for the formation of the crown compounds. In other instances the substituent can be introduced after formation of the macrocyclic ring by conventional chemical reaction, e.g., by azo coupling of an amino compound to introduce the azo grouping. In yet other instances, the substituents can be formed by chemical reaction of other substituents, e.g., nitro groups can be reduced to amino groups.

Typical aldehydes useful in making the crowns of the present invention include: formaldehyde, acetaldehyde, propionaldehyde, n-butyraldehyde, isobutyraldehyde, n-valeraldehyde, isovaleraldehyde, n-hexaldehyde, methylethylacetaldehyde, trimethylacetaldehyde, diethylacetaldehyde, cyclopentylaldehyde, n-heptaldehyde, cyclohexylaldehyde, n-octaldehyde, cyclohexylacetaldehyde, nonaldehyde, decanaldehyde, tridecanaldehyde, myristaldehyde, palmitaldehyde, stearaldehyde, benzaldehyde, phenylacetaldehyde, p-tolualdehyde, 1-naphthaldehyde, 2-anthraldehyde, and 2-furaldehyde.

The cyclic ketones useful in making the crowns of the present invention include cyclobutanone, cyclopentanone, acyclohexanone, cycloheptanone, cyclooctanone, cyclononanone, cyclodecanone, cycloundecanone, cyclododecanone, cyclopentadecanone, cyclooctadecanone, and cycloeicosanone.

Typical diorganodichlorosilanes useful in making the crowns of the present invention include:
    didodecyldichlorosilane
    diethyldichlorosilane
    dimethyldichlorosilane
    dioctyldichlorosilane
    diphenyldichlorosilane
    methylvinyldichlorosilane
    methylethyldichlorosilane
    methyl(propenyl)dichlorosilane
    allylmethyldichlorosilane
    vinylallyldichlorosilane
    ethylpropenyldichlorosilane
    cyclopentadienyl(vinyl)dichlorosilane
    ethylpentyldichlorosilane
    hexylmethyldichlorosilane
    ethyl(m-chlorophenyl)dichlorosilane
    methyl(p-tolyl)dichlorosilane
    ethylphenyldichlorosilane
    methyl(sec-octyl)dichlorosilane
    dihexyldichlorosilane
    dioctadecyldichlorosilane
    allylphenyldichlorosilane
    cyclopentamethylenedichlorosilane
    cyclotetramethylenedichlorosilane
    diallyldichlorosilane
    methyloctadecyldichlorosilane
    phenylmethyldichlorosilane
    phenylvinyldichlorosilane These compounds are described in *Organosilicon Compounds*, Vol. II, Parts 1 and 2, V. Bazant, V. Chvalovsky, and J. Rathowsky, Academic Press, N.Y., 1965.

Typical diorganotin dichlorides useful in making the crowns of the present invention include: diamyltin dichloride; dibenzyltin dichloride; dibutyltin dichloride; diethyltin dichloride; ethylpropyltin dichloride; diisobutyltin dichloride; diisopropyltin dichloride; dimethyltin dichloride; diisoamyltin dichloride; diphenyltin dichloride; benzylphenyltin dichloride; di-m-tolyltin dichloride; dioctyltin dichloride; di-p-biphenyltin dichloride; dipropyltin dichloride; and divinyltin dichloride. Organotin compounds are described in *Handbook of Organometallic Compounds*, H. C. Kaufman, D. van Nostrand Co., Inc., 1961.

EXAMPLE 1

A. Preparation of 2,2'-(Oxydiethylenedioxy)-diphenol, a compound of the structure

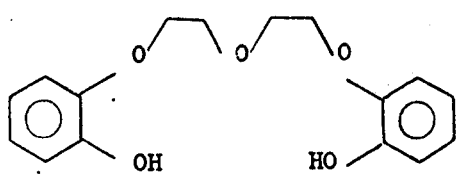

A vigorously agitated mixture of 220 grams (2 grammols) of catechol, 2000 ml. of water, 80 grams (2 gram-mols) of sodium hydroxide and 143 grams (1 grammol) of bis(beta-chloroethyl)ether is reacted at reflux at 102°–103°C. for 16 hours under nitrogen. It is then acidified with concentrated hydrochloric acid. When unreacted bis(2-chloroethyl)ether and 1000 ml. of water have been removed by distillation, the mixture separates into two layers. The organic layer is recovered and treated with 700 ml. of methanol and chilled with ice water. The crystals that subsequently form are filtered off, washed with cold methanol, and dried. The 2,2'-(oxydiethylenedioxy)-diphenol product, 67 to 74 grams (23 to 25.5% yield), melts at 85°C. and analyzes as follows (a typical example.

|  | Calcd. for $C_{16}H_{18}O_5$ | Found |
|---|---|---|
| O:% | 66.2 | 66.2, 66.2 |
| H:% | 6.2 | 5.7, 5.8 |
| Mol. Wt. | 290 | — |

B. Preparation of 2,3,13,14-dibenzo-1,4,7,9,12,15,18-heptaoxacycloeicosane, a compound of the formula

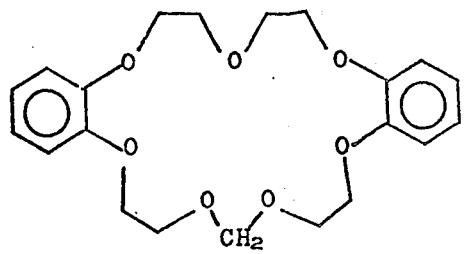

A solution of 9 grams (0.052 gram-mol) of $CH_2(OCH_2CH_2Cl)_2$ in 50 ml. of n-butanol is added over a 2-minute period to an agitated refluxing mixture of 14.5 grams (0.05 gram-mol) of 2,2'-oxydiethylenedioxydiphenol, 4 grams (0.1 gram-mol) of sodium hydroxide in 5 ml. of water, and 150 ml. of n-butanol. The resulting composition is then agitated at reflux for about 18 hours at 107°–108.5°C. The —O—CH$_2$—O—substituted crown 2,3,13,14-dibenzo-1,4,7,9,12,15,18-heptaoxacycloeicosane, which precipitates on cooling as a white solid (12.1 grams), is washed thoroughly with water, dried and recrystallized from p-dioxane as white crystals melting at 151°–152°C. and giving the following analysis:

|  | Calcd. for $C_{21}H_{26}O_7$ | Found |
|---|---|---|
| C:% | 64.6 | 64.1, 64.4 |
| H:% | 6.7 | 6.5, 6.7 |
| Mol. Wt. | 390 | 379, 390 |

The crystals of this crown compound are readily soluble in chloroform, methanol, acetone or water.

C. Hydrolysis of 2,3,13,14-Dibenzo-1,4,7,9,12,15,18-heptaoxacycloeicosane to a diol A mixture containing 2 grams (0.005 gram-mol) of the crown compound made in Part B above, 5 ml. of concentrated hydrochloric acid, and 5 ml. of water is agitated at reflux until all the white solid has disappeared (typically requiring 7 min.). Removal of volatiles under vacuum gives a white waxy solid, which on recrystallization from benzene, yields 1.5 grams of white solid having the following analysis:

|  | Calcd. for $C_{20}H_{28}O_7 \cdot 2H_2O$ | Found |
|---|---|---|
| C:% | 58.0 | 58.8, 59.0 |
| H:% | 7.2 | 7.3, 7.3 |
| Mol. Wt. | 414 | 427 |

The hydrolysis product is named 2,2′ [oxydiethylenedioxydi-(o-phenylene)dioxy]-diethanol (this compound may also be named 4,5,13,14-dibenzo-3,6,9,12,15-pentaoxaheptadecane-1,17-diol) and has the formula

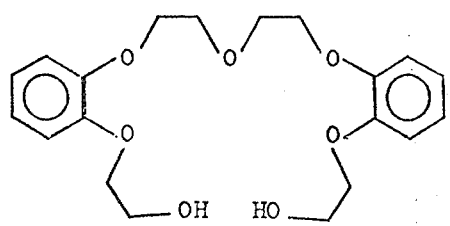

EXAMPLE 2

Preparation of 2,3,13,14-dibenzo-1,4,7,9,12,15,18-heptaoxa-8-sulfinyleicosane, a compound of the formula

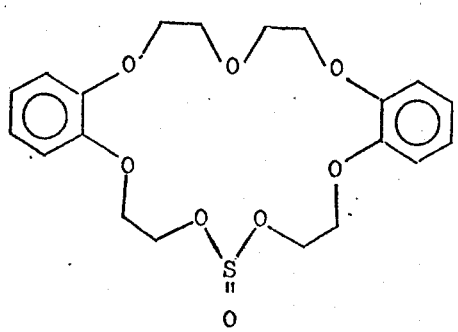

After the hydrolyzed crown compound made in Part C of Example 1 (1.89 grams, 0.005 gram-mol) has been dissolved in 200 ml. of warm benzene on a steam bath, 3.14 grams (3.2 ml., 1.04 gram-mol) of pyridine and 1.2 grams (0.74 ml., 0.01 gram-mol) of thionyl chloride are added. The resulting white precipitate of pyridine hydrochloride is removed and the benzene filtrate is washed with 150 ml. water and 5 ml. conccentrated hydrochloric acid, dried, and evaporated to give the >S=O substituted crown compound 2,3,13,14-dibenzo-1,4,7,9,12,15,18-heptaoxa-8-sulfinyl-eicosane. Recrystallization from a mixture of benzene and cyclohexane produces white crystals melting at 133°C. and analyzing as follows:

|  | Calcd. for $C_{20}H_{24}O_8S$ | Found |
|---|---|---|
| C:% | 56.6 | 56.7, 56.8 |
| H:% | 5.7 | 5.8, 6.0 |
| S:% | 7.5 | 6.4 |

EXAMPLE 3

Preparation of 2,3,13,14-dibenzo-8-carbonyl,1,4,7,9,12,15,18-heptaoxaeicosane, a compound of the formula Gaseous phosgene (122 ml., 0.005 gram-mol) is passed through a solution of 1.89 grams (0.005 gram-mol) of the hydrolyzed crown compound made in Part C of Example 1 and 1.58 grams (1.61 ml., 0.07 gram-mol) of pyridine in 200 ml. of benzene at 36°C. The resulting mixture is heated to 70°C., pyridine hydrochloride precipitate is filtered off, and the benzene filtrate is evaporated to give the >C=O substituted crown compound 2,3,13,14-dibenzo-8-carbonyl-1,4,7,9,12,15,18-heptaoxaeicosane as a glass (1.5 grams) which crystallizes on standing. Recrystallization from methanol gives white crystals melting at 122°–125°C. and analyzing as follows:

|  | Calcd. for $C_{21}H_{24}O_8$ | Found |
|---|---|---|
| C:% | 62.4 | 62.1, 62.1 |
| H:% | 5.9 | 6.0, 6.1 |

EXAMPLE 4

Preparation of 2,3,13,14-dibenzo-1,4,7,9,12,15,18-heptaoxa-8,8-pentamethylene-cycloeicosane, a compound of the formula

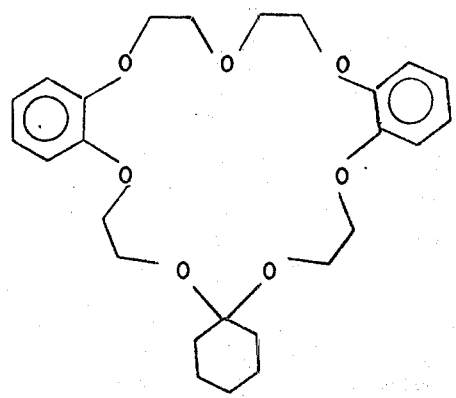

A solution of 4.14 grams (0.01 gram-mol) of the hydrolyzed crown compound made in Part C of Example 1, 9.8 grams (0.1 gram-mol) of cyclohexanone, and a saturation concentration (a little less than 0.2 gram) of p-toluene sulfonic acid monohydrate in 400 ml. of benzene is agitated on a steam bath while the benzene is partly distilled off to complete the reaction by removing the by-product water. Another portion of benzene (150 ml.) is added. After about 5.5 hours the warm benzene solution is washed with a solution of 5 grams of sodium bicarbonate in 200 ml. of water to remove the p-toluene sulfonic acid. After a cold water wash, the solution is allowed to stand for about 16 hours. The white precipitate (hydrolyzed crown compound) now present is filtered off and the benzene filtrate evaporated to yield the desired ketal substituted crown compound 2,3,13,14-dibenzo-1,4,7,9,12,15,18-heptaoxa-8,8-pentamethylene-cycloeicosane, a white solid. After purification by trituration with cold methanol and drying, it is recrystallized from methanol. The shiny crystals, which result, melt at 162°C. and analyze as follows:

|  | Calcd. for $C_{26}H_{34}O_7$ | Found |
|---|---|---|
| C:% | 68.1 | 67.8 |
| H:% | 7.4 | 7.1 |

EXAMPLE 5

A. Preparation of 2,2'-Trimethylenedioxydiphenol

The mono-bridged 2,2'-trimethylenedioxydiphenol is made in accordance with Example 1 of U.S. Patent 3,361,778 to Pedersen using catechol in place of its tert-butyl derivative.

B. Preparation of 2,3,13,14-Dibenzo-1,3,7,9,12,15-hexaoxacyclooctadecane, a compound of the formula

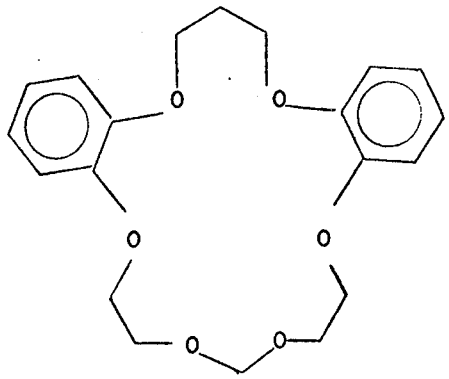

The procedure used is like the one described in Part B of Example 1 except that the diphenol is changed.

A 14.4 gram (0.083 gram-mol) portion of $(ClCH_2CH_2O)_2CH_2$ is added to an agitated solution made by mixing 21.5 grams (0.083 gram-mol) of 2,2'-trimethylenedioxydiphenol, 10.7 grams (0.166 gram-mol) of 85% potassium hydroxide, and 600 ml. of 1-butanol. After being refluxed for a total of 23 hours, the solution is decanted from precipitated potassium chloride and evaporated. The residue (20.9 grams) is dissolved in 300 ml. methylene chloride and the solution washed free from unreacted diphenol with 200 ml. portions of aqueous sodium hydroxide, dried, and evaporated to give the —O—CH₂—O—substituted compound 2,3,13,14-dibenzo-1,4,7,9,12,15-hexaoxacyclooctadecane (15.2 grams). The crown compound is recrystallized from methanol as a pale yellow solid. One portion is recrystallized from n-heptane to give a white crystal analyzing as follows:

|  | Calcd. for $C_{20}H_{24}O_6$ | Found |
|---|---|---|
| C:% | 66.7 | 67.7 |
| H:% | 6.7 | 7.1 |
| Mol. Wt. | 360 | 378 |

The rest of the pale yellow solid is heated with methanolic HCl to decompose the —O—CH₂—O— group and form —O—CH₂—CH₂—OH groups on each benzene ring. The diol 2,2'-[trimethylenedioxy-di(o-phenylene)dioxy]-diethanol is obtained as a brownish glass analyzing as follows:

|  | Calcd. for $C_{19}H_{24}O_6$ | Found |
|---|---|---|
| C:% | 65.5 | 65.2 |
| H:% | 6.9 | 7.0 |
| Mol. Wt. | 348 | 319 |

EXAMPLE 6

One-Step Preparation of 2,3,13,14-Dibenzo-1,4,7,9,12,15,18,20-Octaoxadocosane, a compound of the formula

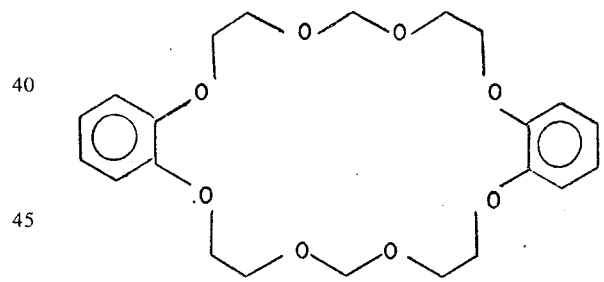

In the following procedure the +O—CH₂CH₂—O)₂CH₂ bridged diphenol is made in situ and used as a reactant without being isolated.

During a period of about one hour a solution of 18 grams (0.104 gram-mol) of $CH_2(O—CH_2—CH_2Cl)_2$ in 20 ml. of n-butanol is added dropwise to an agitated, refluxing (111–113° C.) solution made by mixing 22 grams (0.2 gram-mol) of catechol, 8 grams (0.2 gram-mol) of sodium hydroxide and 150 ml. of n-butanol. The dropwise addition is repeated during a second one-hour period. The resulting mixture is then agitated at 111°–112° C. for 16 hours. Evaporation under vacuum gives about 38.1 grams of solid (theory 42.0 grams). Any unreacted catechol and diphenol are removed by dissolving this solid in chloroform and extracting with 5% sodium hydroxide (aqueous). The —O—CH₂—O— disubstituted crown compound 2,3,13,14-dibenzo-1,4,7,9,15,18,20-octaoxadocosane is obtained as a semi-solid weighing 25.6 grams. It recrystallizes from p-dioxane as near white crystals melting at 166°–167° C. and analyzing as follows:
|  | Calcd. for $C_{22}H_{28}O_8$ | Found |
|---|---|---|
| C:% | 62.8 | 62.9, 63.1 |
| H:% | 6.7 | 6.7, 6.9 |
| Mol. Wt. | 420 | 435, 435 |
I claim:
1. Macrocyclic polyether compounds of the formula
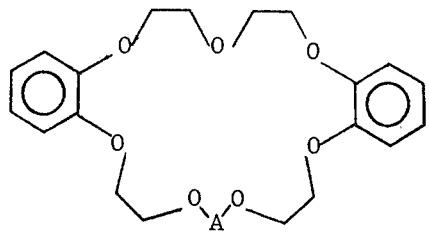
where
A is
or —CH$_2$—.
2. The compound of claim 1 wherein A is —CH$_2$—.
3. The compound of claim 1 wherein A is
* * * * *